(12) United States Patent
Maschke

(10) Patent No.: US 8,241,199 B2
(45) Date of Patent: Aug. 14, 2012

(54) BLOOD PUMP, MEDICAL APPARATUS HAVING A BLOOD PUMP AND METHOD FOR ASSISTING THE POSITIONING OF A BLOOD PUMP

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 236 days.

(21) Appl. No.: 12/728,484

(22) Filed: Mar. 22, 2010

(65) Prior Publication Data

US 2010/0240944 A1 Sep. 23, 2010

(30) Foreign Application Priority Data

Mar. 23, 2009 (DE) .......................... 10 2009 014 462

(51) Int. Cl.
*A61N 1/00* (2006.01)
(52) U.S. Cl. .......................................... 600/16; 600/427
(58) Field of Classification Search .............. 600/16–18, 600/411, 424–427
See application file for complete search history.

(56) References Cited

U.S. PATENT DOCUMENTS

| | | | |
|---|---|---|---|
| 6,377,048 B1 | 4/2002 | Golan et al. | |
| 6,600,319 B2 | 7/2003 | Golan | |
| 6,659,940 B2 | 12/2003 | Adler | |
| 7,087,023 B2 | 8/2006 | Daft | |
| 2003/0097048 A1 | 5/2003 | Bouma | |
| 2006/0103850 A1 | 5/2006 | Alphonse | |
| 2007/0156006 A1* | 7/2007 | Smith et al. ..................... | 600/16 |
| 2008/0133006 A1* | 6/2008 | Crosby et al. ................ | 623/3.13 |

FOREIGN PATENT DOCUMENTS

| | | |
|---|---|---|
| AT | 6847 U2 | 5/2004 |
| DE | 19852467 A1 | 7/1999 |
| DE | 10040403 A1 | 2/2002 |
| DE | 10336902 B3 | 8/2004 |
| DE | 102004015641 B3 | 3/2006 |
| DE | 102004049986 A1 | 4/2006 |
| DE | 102004058008 A1 | 6/2006 |
| WO | WO 9409835 A1 | 5/1994 |
| WO | WO 0111409 A2 | 2/2001 |

OTHER PUBLICATIONS

A. Arena et al.; "Intercorporeal Videoprobe (IVP)"; Medical and Care Compunetics 2, L. Bos et al. (Eds) IOS Press, 2005, p. 167; pp. 1-8.
H. Lim et al.; "Optical frequency domain imaging with a rapidly swept laser in the 815-870 nm range"; Jun. 26, 2006; vol. 14, No. 13; Harvard Medical School and Wellman Center for Photomedicine, Massachusetts 02114. R.J. Dickinson, R.I. Kitney; "Miniature ultrasonic probe construction for minimal access surgery"; Department of Bioengineering, Imperial College, London; Institute of Physics Publishing; Physics in Medicine and Biology (Phys. Med. Biol. 49 (2004), pp. 3527-3538.; London.
Christoph Kuratli; "Realization of Silicon Based Ultrasound Micro-Systems"; Dissertation (Swiss Federal Institute of Technology Zurich); St. Gallen; 1999; pp. i-ix and 1-116.
Dipl.-Ing. (FH) CH.Benk; "IMPELLA Ein intrakardiales Blutpumpensystem", Abt. Herz- und Gufäβchirurgie, Herz-Kreislauf Zentrum Albert-Ludwigs-Universität Freiburg, 2009.
T.Siess, C.Nix, D.Michels, "Story I: Impella—Eine Erfolgsgeschichte mit Achterbahnfahrt", E. Wintermantel S.-W. Ha, Medizintechnik—Life Science Engineering. DOI: 10.1007/978-3-540-74925-7, Springer 2008; p. 1617.
"Kompetenznetze Deutschland, networking for innovation", pp. 1-3; Retrieved online Jan. 19, 2009; file:// C:\DOCUME~1\e040273a\LOCALS~1\Temp\0WOEF4U0.htm.
Medknowledge; Retrieved online Jan. 12, 2009; pp. 1-5; file: //E:\Minimalinvasive Herzpumpe Impella Recover Lp 2,5.htm.

* cited by examiner

Primary Examiner — Scott Getzow

(57) ABSTRACT

The invention relates to a blood pump and a medical apparatus having a blood pump, which is provided for insertion into the heart of a patient. The blood pump has at least one imaging sensor disposed in the region of the distal end of the blood pump to obtain imaging information in a blood vessel or in the heart. The invention also relates to a method for assisting the positioning of a blood pump in the heart of a patient, wherein image information is recorded inside the body of the patient using the at least one imaging sensor of the blood pump and transmitted in real time to an image processing and playback facility disposed outside the body of the patient for display purposes.

10 Claims, 4 Drawing Sheets

BLOOD PUMP, MEDICAL APPARATUS HAVING A BLOOD PUMP AND METHOD FOR ASSISTING THE POSITIONING OF A BLOOD PUMP

CROSS REFERENCE TO RELATED APPLICATIONS

This application claims priority of German application No. 10 2009 014 462.5 filed Mar. 23, 2009, which is incorporated by reference herein in its entirety.

FIELD OF THE INVENTION

The invention relates to a blood pump as well as a medical apparatus having a blood pump, which is provided for insertion into the heart of a patient. The invention also relates to a method for assisting the positioning of a blood pump in the heart of a patient.

BACKGROUND OF THE INVENTION

Cardiac disease is one of the most common causes of death in the industrial world. Many patients with cardiac disease have to be given a donor heart, which generally involves a waiting period. During the waiting period for a donor heart, a number of patients were given artificial hearts with the use of heart-lung machines but this is no longer common practice for a number of reasons, among them the fact that the intervention is risky and expensive.

To preserve the heart, more complex operations are now carried out increasingly on the beating heart, in particular to avoid the use of heart-lung machines and the associated side effects for the patient. For some years now blood pumps have been used during such operations, to assist the pumping function of the heart before, during and after the heart operation. Such blood pumps are also known as left ventricular and right ventricular Impella blood pumps. Such a blood pump can be positioned percutaneously by way of the vascular system, for example in a ventricle, with the aid of a catheter in order to provide an additional pumping function to the heart there. Impella blood pumps are so small that they can be positioned in the heart both directly by way of the aorta or vena cava as well as through the leg artery or vein. Such intracardiac Impella blood pumps are described in DE 100 40 403 A1, DE 103 36 902 B3 and DE 10 2004 049 986 A1.

A left ventricular Impella blood pump is inserted into the aorta with the aid of the catheter and advanced into the left ventricle by way of the aortic valve. The blood is conveyed out from the ventricle through a tube and exits again in the aorta at the pump.

In the case of the right ventricular Impella blood pump access is by way of the vena cava superior. A tube is then inserted through the right atrium and the ventricle by way of the pulmonary valve into the truncus pulmonalis. The blood is conveyed out from the atrium through the tube and exits again at the opening of the tube in the truncus pulmonalis.

The biventricular intracardiac pump system—Impella—replaces extracorporeal blood circulation and therefore the use of a heart-lung machine during minimally invasive coronary surgery. The system reduces the invasive nature of the intervention and provides better protection for the heart.

Today an Impella blood pump is positioned in the heart of a patient using x-ray radiation, in other words the advance of the Impella blood pump through one or more blood vessels, the insertion of the Impella blood pump into the heart and the correct positioning of the Impella blood pump in the heart are controlled by x-ray. The correct location of the Impella blood pump in the heart during its operation must also be monitored or controlled at least from time to time by means of x-ray radiation after the medical intervention.

SUMMARY OF THE INVENTION

The object of the invention is to specify a blood pump, a medical apparatus and a method of the type mentioned in the introduction such that the advance of the blood pump and/or the positioning of the blood pump in the heart of a patient can take place where possible without x-ray radiation or at least with reduced application of x-ray radiation.

According to the invention this object is achieved by a blood pump for insertion into the heart of a patient, having at least one imaging sensor disposed in the region of the distal end of the blood pump.

While the blood pump is being advanced in a blood vessel or during the positioning of the blood pump in the heart of a patient it is possible to use the at least one imaging sensor to record image information from the interior of the blood vessel or the interior of the heart and use said information to control the blood pump as it is advanced or positioned in the heart. The image information obtained with the imaging sensor makes it possible largely to dispense with the x-ray fluoroscopy used per se to handle, position and control the location of the blood pump, said x-ray fluoroscopy being a concern not only for the patient but also for the medical staff handling the blood pump.

The at least one imaging sensor is preferably disposed within an outer sheath of the blood pump in the region of the distal end of the blood pump. This allows a relatively precise and high-resolution display of the space around the distal end of the blood pump. The imaging sensor can be used to transmit "live images" from the site of the minimally invasive intervention, i.e. directly from the blood vessel or heart, to an externally disposed image processing and playback facility, e.g. a computer-controlled visualization system with attached monitor. The insertion and advance of the blood pump into or through the blood vessel(s) and precise positioning of the blood pump in the heart can be tracked and monitored in real time. The high resolution location image thus achieved allows fine position corrections to be made to the blood pump in a timely manner.

X-ray checks can also be recorded at selected times as required to complement imaging with the aid of the blood pump.

According to one variant of the invention the at least one imaging sensor is configured and/or aligned so that its image recording region at least partially covers a spatial region around the distal end of the blood pump, in particular a spatial region around the distal end of the outer cylindrical tube-type sheath of the blood pump. In other words the at least one imaging sensor "looks" essentially radially outward—in relation to the center axis of the outer cylindrical tube-type sheath of the blood pump—so that the image recording region is essentially annular.

According to another variant of the invention the at least one imaging sensor is configured and/or aligned so that its image recording region at least partially covers the spatial region in front of the distal end of the blood pump, in particular the spatial region in front of the distal end of the outer cylindrical tube-type sheath of the blood pump. The imaging sensor therefore "looks" forward in relation to the advance of the blood pump, which is expedient when monitoring the advance of the blood pump and its positioning.

Ideally the two possibilities set out above are combined in an appropriate manner for the at least one imaging sensor, so that the sensor has the largest possible image recording region both in a radial and in a forward direction. Alternatively, if space allows, a number of imaging sensors can also be provided, which cover different spatial angle regions in a complementary manner.

According to one embodiment of the invention the at least one imaging sensor can be displaced longitudinally in relation to the outer cylindrical tube-type sheath of the blood pump. For example provision can be made to move the at least one imaging sensor out from a "retracted" stop position in the region of the distal end of the outer sheath in a forward direction out of the outer sheath, in order in so doing, with the outer sheath of the blood pump in a constantly maintained position, to define an observation point with a variety of positions, from which it is possible to view the tissue regions further ahead or in front of the blood pump. To this end the imaging sensor can be disposed for example on an inner catheter that can be displaced relative to the outer sheath of the blood pump and is disposed in its hollow space or on an inner part.

According to variants of the invention the at least one imaging sensor is in the form of an (acoustic) ultrasonic sensor, a magnetic resonance sensor or an optical image sensor, in particular a CMOS image sensor, an OCT image sensor, an LCI image sensor, an MR image sensor or an OFDI image sensor.

Ultrasound imaging (sonography) is based on the so-called echo-pulse method. An electric pulse from a high-frequency generator is converted in the sound head of an ultrasonic transducer (generally a piezo-crystal but a silicon-based sensor is also possible) to a sound pulse and output. The sound wave is partially or completely scattered or reflected at the inhomogeneities of the tissue structure. A returning echo is converted to an electric signal in the sound head and then visualized in an attached electronic evaluation and display unit, it being possible for mechanical or electronic pivoting of the sensor to produce a 2D or 3D scan of the examination region. Intravascular ultrasound imaging (IVUS) is particularly suitable for imaging deeper tissue layers and vascular structures.

However the imaging sensor can also be a so-called IVMRI sensor for intravascular magnetic resonance tomography (IVMRI=Intra Vascular Magnetic Resonance Imaging). During magnetic (nuclear) resonance tomography the magnetic moments (nuclear spin) of the atomic nuclei of the examined tissue are aligned in an external magnetic field and excited by irradiated radio waves to perform a gyroscopic movement (precession), with an electrical magnetic resonance signal being induced further to relaxation processes in an assigned receive coil and forming the basis for image calculation.

Recently it has become possible to miniaturize the magnetic field generating elements and the transmit and receive coils and integrate then in an imaging IVMRI sensor so that an intracorporeal or intravascular application of the MRI method (MRI=Magnetic Resonance Imaging) is possible, with the necessary static magnetic field advantageously being generated or applied within the body of the patient. Such a concept is described for example in U.S. Pat. No. 6,600,319.

To this end a permanent magnet or an electromagnet for generating a static magnetic field and a coil that acts equally as a transmit and receive coil are integrated in the IVMRI sensor. The magnet generates field gradients of preferably 2 T/m to 150 T/m in proximity to the vessel or organ to be examined. In proximity here means up to 20 mm away from the magnet. Radio waves in the frequency range from 2 MHz to 250 MHz to excite the surrounding body tissue can be decoupled by way of the coil as a function of the strength of the magnetic field. Higher static magnetic field strengths require higher frequencies in the excitation field. The coil advantageously also serves to receive the associated "response field" from the body tissue. In an alternative embodiment separate transmit and receive coils can be provided.

In contrast to conventional MRI systems the IVMRI sensor and the electronic switching circuits and digital evaluation units provided for signal processing and evaluation are advantageously designed so that they can operate with high local field gradients and generate corresponding magnetic resonance images even with a relatively inhomogeneous magnetic field. Since in such conditions the received echo signals are influenced in a characteristic manner by the microscopic diffusion of water molecules in the examined tissue, it is generally possible to achieve an excellent visualization and differentiation between different soft parts, e.g. between lipid layers and fibrous tissue. This is of particular relevance, especially in the field of application of minimally invasive interventions now provided for. It is known from more recent studies that the typical infarction regions in the heart in particular can be visualized clearly using MRI.

As an alternative to the concept described here, the static magnetic field can also be generated by means of external magnets. In contrast to conventional MRI however the dynamic fields, i.e. the radio waves, are expediently generated intravascularly in this embodiment also, i.e. by means of a number of transmit and receive units disposed on the blood pump.

In an alternative or additional embodiment, an optical imaging sensor can also be provided. For example an optical semiconductor detector based on the known CMOS technology (CMOS=Complementary Metal Oxide Semiconductor) can be considered suitable for detecting incident light. Like the CCD sensors (CCD=Charge-Coupled Device) known principally from the field of digital photography, such a CMOS sensor, also known as an "active pixel sensor", is based on the internal photoelectric effect and as well as having a low current consumption also possesses the advantage that it is particularly cheap to manufacture. With this imaging variant, a suitable light source, e.g. an LED (LED=Light Emitting Diode), must be provided in the region of the distal end of the blood pump for the purpose of illuminating the examination and treatment region, it being possible for said light source to be supplied with electric current by way of an electrical line routed through the blood pump.

In a further variant the blood pump can also be equipped with an OCT sensor (OCT=Optical Coherence Tomography).

Optical coherence tomography imaging delivers high-resolution images which reproduce in particular the structures in proximity to the vessel surface relatively accurately. The principle of this method is based on the fact that light, preferably infrared light, supplied by the blood pump by way of an optical waveguide is beamed into the vessel or onto a tissue structure, the light reflected there being coupled back into the optical waveguide and routed to an evaluation facility. In the evaluation unit—as in the case of a Michelson interferometer—the interference of the reflected light with the reference light is analyzed in order to generate the image.

Whereas conventional interferometric equipment preferably operates with laser light of a defined wavelength, which possesses a relatively great optical coherence length, with so-called LCI (LCI=Low Coherence Interferometry) light sources with broadband radiation characteristics ("white light") and with a relatively low coherence length of the emitted light are used. Corresponding image sensors which are now provided according to an advantageous embodiment of the invention for use in the blood pump are described for example in US 2006/0103850 A1.

In a further modification an image sensor can also be provided which is based on the so-called OFDI principle (OFDI=Optical Frequency Domain Imaging). This method is related to OCT, but uses a wider frequency band. The operating principle is described in more detail e.g. in the publication "Optical frequency domain imaging with a rapidly swept laser in the 815-870 nm range", H. Lim et al., Optics Express 5937, Vol. 14, No. 13.

Finally the blood pump can also have an imaging sensor, which is based on what is known as "Near-Infrared (NIR) Diffuse Reflectance Spectroscopy".

Combinations of at least two optical sensors of the type mentioned above can also be present.

A tabular overview summarizes the strengths and weaknesses of the respective optical imaging methods (from ++=particularly good or suitable, to −−=deficient or unsuitable):

| Comparison of image sensors | Near resolution | Far resolution | Penetration of blood |
|---|---|---|---|
| Optical (CMOS) | + | + | − |
| OCT | ++ | − | −− |
| LCI | + | + | + |
| NIR | − | − | +/− |
| OFDI | ++ | − | + |

Since the spatial angle that can be detected or has to be overseen using the respective optical image sensor is generally limited, it is advantageous, particularly with the configuration mentioned above with a radial viewing direction in relation to the center axis of the outer sheath of the blood pump, if according to one variant of the invention the imaging sensor can be rotated by way of a drive shaft, which is preferably passed through a hollow space in the blood pump, in particular in relation to the outer sheath of the blood pump. By this means it is possible to obtain a 360° panoramic view without the need to rotate the outer sheath of the blood pump or the blood pump itself relative to its surroundings within the body.

According to one variant of the invention the blood pump has a drive shaft, which both drives a pump wheel of the blood pump to pump blood and is also provided to rotate the at least one imaging sensor. To this end the drive shaft is preferably assigned a microtransmission, which is used to provide an appropriate rotational speed to rotate the imaging sensor.

Alternatively it is also conceivable to dispose a plurality of imaging sensors or sensor elements in a line or ring, for example distributed over the circumference of the outer sheath and preferably looking outward and to provide a cyclical data readout from the imaging sensors, e.g. by way of a multiplexer. Such a configuration is achieved for example by disposing the imaging sensors in a fixed manner on/along the outer sheath of the blood pump. Alternatively or in addition to this the or additional imaging sensors can also be disposed in groups within the outer sheath. They can advantageously be displaced longitudinally—optionally as sensor clusters or separately. With such a configuration only a single signal line is required within the outer sheath, by way of which the image data of the various imaging sensors is sent or interrogated sequentially in the manner of a serial interface. A small number of signal lines, preferably just the one, limits the amount of space required here within the outer sheath of the blood pump.

By mechanical or electronic rotation of the image sensor with simultaneous retraction or advance it is advantageously possible to generate 3D recordings or volume data records by means of appropriate signal processing and image calculation methods known in principle from the prior art.

In one advantageous development of the invention at least one position sensor of a position detection system is preferably disposed in the region of the distal end of the outer sheath of the blood pump, in order to enable the current position and/or the current location of the blood pump within the body of the patient to be determined. Generally the position sensor comprises a number of electromagnetic transmit coils which interact with a number of receive coils or signal detectors disposed externally, i.e. outside the patient.

In an alternative embodiment the roles of the transmit and receive units can also be reversed; in other words the receive coils are fixed on or in the blood pump while the transmit coils are preferably disposed in a stationary manner in space.

In a further expedient embodiment the blood pump has at least one passive sensor, for example an RFID transponder (RFID=Radio Frequency Identification). A response signal is generated in the RFID transponder from a signal transmitted from a stationary receive coil, said response signal being received by a stationary receive coil and allowing precise spatial location of the RFID transponder. A passive sensor thus does not need its own energy supply and therefore advantageously no supply line from outside.

Instead of electromagnetic position sensors it is also possible to use ultrasonic sensors as position sensors, these being part of a position detection system based on ultrasonic waves. Such a position detection system and its function are described in DE 198 52 467 A1, the disclosure of which in this respect should be included in the present application. In this instance one ultrasonic transducer should be provided on the blood pump and four or more reference ultrasonic transducers should preferably be provided outside the body of the patient P, in order to be able to determine the respective position and location of the blood pump from distance measurements.

The position data obtained from the position sensor on the one hand facilitates the safe insertion of the blood pump and its navigation to the heart; on the other hand it advantageously assists the construction of three-dimensional recordings from a plurality of two-dimensional cross-sectional images. The position data can also advantageously be used in the computational correction of motion artifacts and the like.

The object underlying the invention is also achieved by a medical apparatus having a blood pump as described above and an image processing and playback facility, the at least one imaging sensor of the blood pump being connected by way of at least one signal line to the image processing and playback facility disposed outside the blood pump and the body of the patient and it being possible for image information recorded using the at least one imaging sensor to be transmitted to this in real time, so that the advance or positioning of the blood pump in the heart can be controlled based on current image information.

The object underlying the invention is also achieved by a method for assisting the positioning of a blood pump as described above in the heart of a patient, wherein image information is recorded inside the body of the patient using the at least one imaging sensor of the blood pump and transmitted in real time to an image processing and playback facility disposed outside the body of the patient. The image information transmitted in real time to the image processing and playback facility makes it possible to monitor and control the advance of the blood pump and/or the positioning of the blood pump in the heart of the patient.

BRIEF DESCRIPTION OF THE DRAWINGS

Exemplary embodiments of the invention are illustrated in the accompanying schematic drawings, in which.

DETAILED DESCRIPTION OF THE INVENTION

Figure 1:
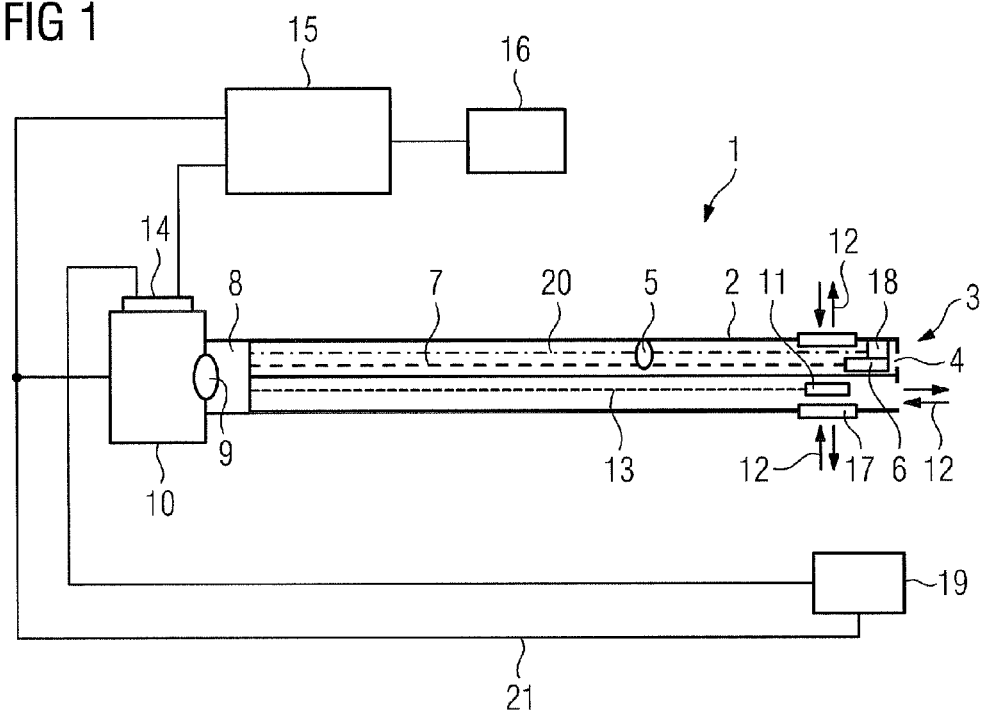
FIG. 1 shows a medical apparatus with a blood pump shown in a longitudinal cross section, having an imaging sensor for insertion into the heart of a patient.

Parts or components of the inventive blood pump and the inventive medical apparatus having at least essentially the same structure and function are shown with the same reference characters in all the figures.

The inventive blood pump 1 shown in a simplified and schematic manner in FIG. 1 is provided for insertion into the heart of a patient in a minimally invasive intervention. In the case of the present exemplary embodiment of the invention the blood pump 1 is preferably an Impella blood pump as mentioned in the introduction.

In the case of the present exemplary embodiment of the invention the blood pump 1 comprises an outer cylindrical tube-type sheath 2, at the distal end 3 of which inflow openings 4 for blood are present. The inflow openings 4 are connected by way of a flow line (not shown in detail) to outlet openings 5 for blood. A schematically illustrated pump wheel 6 is used to convey the blood, i.e. to take in the blood by way of the inflow openings 4, to pump the blood through the flow line and out of the outlet openings 5, said pump wheel 6 being driven either by an electric motor disposed in the blood pump 1 or, as in the present exemplary embodiment of the invention, by means of a drive shaft 7.

The drive shaft 7 is connected by way of a mechanical/electrical connecting unit 8, which has at least one rotary coupling 9 for connectors, to a drive and control unit 10 of the blood pump 1; in other words a drive (not shown in detail) of the drive and control unit 10 causes the drive shaft 7 and therefore also the pump wheel 6 to rotate in a controlled manner by way of the rotary coupling 9.

Figure 2:
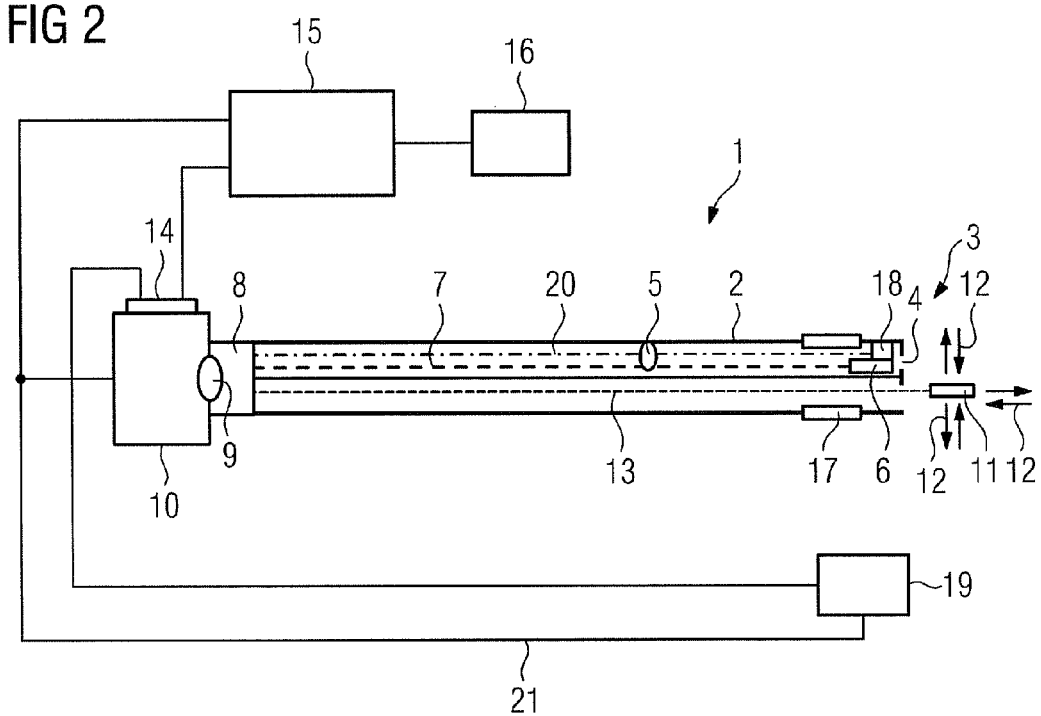
FIG. 2 shows the blood pump from FIG. 1 with a longitudinally displaced imaging sensor.

In contrast to known Impella blood pumps the blood pump 1 has an imaging sensor 11 in the distal end 3 of the outer sheath 2, said imaging sensor 11 being disposed in such a manner that it can be displaced longitudinally relative to the outer sheath 2 in the present exemplary embodiment of the invention. In FIG. 2 the imaging sensor 11 is shown in a longitudinally displaced position. Depending on the sensor type and other details of the embodiment, the image recording region of the imaging sensor 11 is preferably directed radially outward to the vessel wall (not shown in detail) enclosing the blood pump 1 and/or in a forward direction, in other words in the direction of advance of the blood pump 1, as shown symbolically by the arrows 12.

The imaging sensor 11 can be for example an optical or acoustic (ultrasonic) imaging sensor or an imaging sensor based on the principle of magnetic resonance. The signal and supply lines 13 required for its operation and to transmit the recorded image data are guided in the interior of the outer sheath 2 to the rotary coupling 9 of the connecting unit 8, which is connected to the drive and control unit 10. The drive and control unit 10 is connected by way of a signal interface 14 to an external image processing and playback facility 15, to which the image information recorded using the imaging sensor 11 is transmitted to be processed and played back on a monitor 16. This allows image information recorded in an intravascular or intracorporeal manner by the imaging sensor 11 to be displayed on the monitor 16 as "live images" from the site of the blood pump 1, in some instances only after computational processing.

In order to be able to allow the imaging sensor 11 to rotate about its own axis within the outer sheath 2 and relative to the outer sheath 2, a further rotatable drive shaft can also be disposed in the outer sheath 2 but this is not shown in detail in FIG. 1. In contrast to the structure shown in FIGS. 1 and 2 the drive shaft and the imaging sensor 11 here can also be disposed centrally, in other words essentially on the center axis of the outer sheath 2 of the blood pump 1. In particular when interferometric imaging methods are used, optical waveguides can also be positioned in the outer sheath 2 to conduct incident and outward light beams to an externally located interferometer unit or the like, which can be connected by way of the rotary coupling 9 and optionally the signal interface 14. In the region of the imaging sensor 11 the outer sheath 2 has an annular region 17 that is transparent for the respective imaging method and optionally also an optical lens.

In the case of the present exemplary embodiment of the invention an electromagnetic position sensor 18 is disposed in a defined manner in the region of the distal end 3 of the outer sheath 2 of the blood pump 1 in addition to the imaging sensor 11, said electromagnetic position sensor 18 interacting with an electromagnetic position identification unit 19 outside the body of the patient according to the transmitter/receiver principle to allow precise siting or location of the distal end 3 of the outer sheath 2 by identifying the coordinates of the position sensor 18. The position data thus obtained can be supplied for example to the image processing and playback facility 15 and be taken into account during image reconstruction, specifically during artifact correction. The necessary signal lines 20 for the position sensor 18 run through the outer sheath 2, the rotary coupling 9 and the signal interface 14 to the position identification unit 19.

In the case of the present exemplary embodiment of the invention the drive and control unit 10 of the blood pump 1, the image processing and playback facility 15 and the position identification unit 18 are attached to a common data bus 21 for data exchange purposes. Data storage units for image data obtained using the imaging sensor 11, supply and actuating units for the imaging sensor 11 and a user interface with software menus for operating the blood pump 1, the imaging sensor 11 or to assist with diagnosis can also be attached to the data bus 21.

Figure 3:
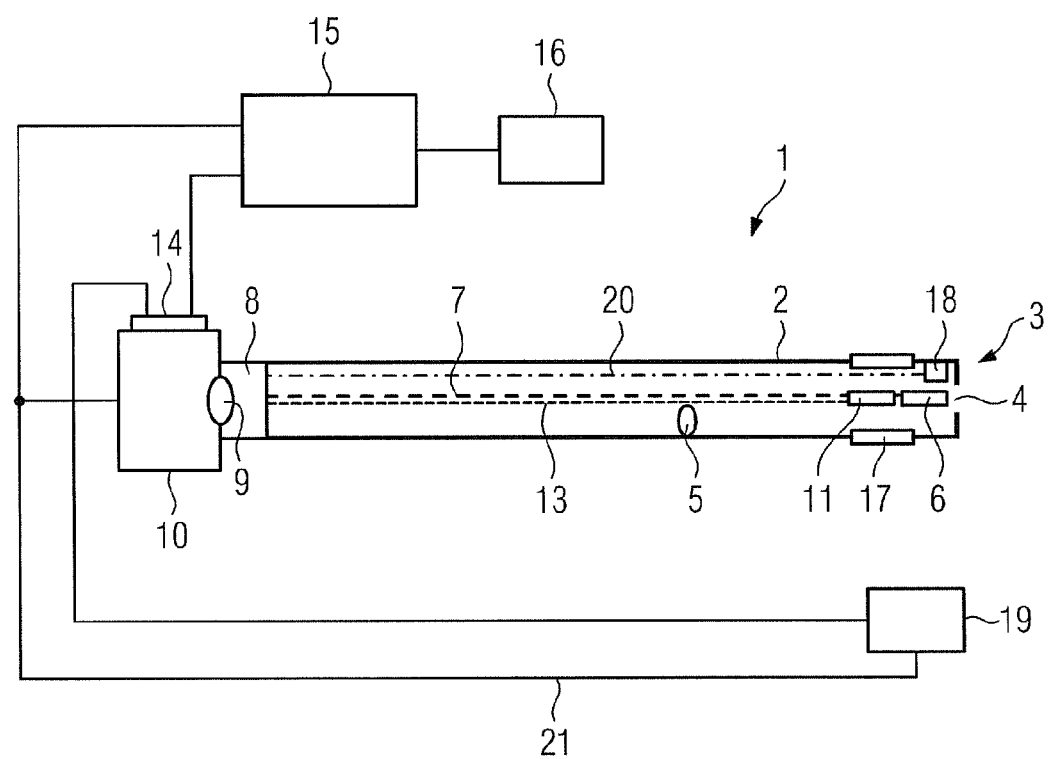
FIG. 3 shows a medical apparatus with a blood pump shown in a longitudinal cross section, having a common drive shaft for a pump wheel of the blood pump and an imaging sensor.

FIG. 3 shows a variant of the blood pump 1, in which only one drive shaft 7 is present, being used both to drive the pump wheel 6 and also to rotate the imaging sensor 11. Since the rotational speed of the drive shaft 7 is too high to rotate the imaging sensor 11, a microtransmission (not shown in FIG. 3) is present, which can be used to supply an appropriate rotational speed to rotate the imaging sensor 11.

FIG. 4-11 show various imaging sensors 11, which can be used in the blood pump 1.

Figure 4:
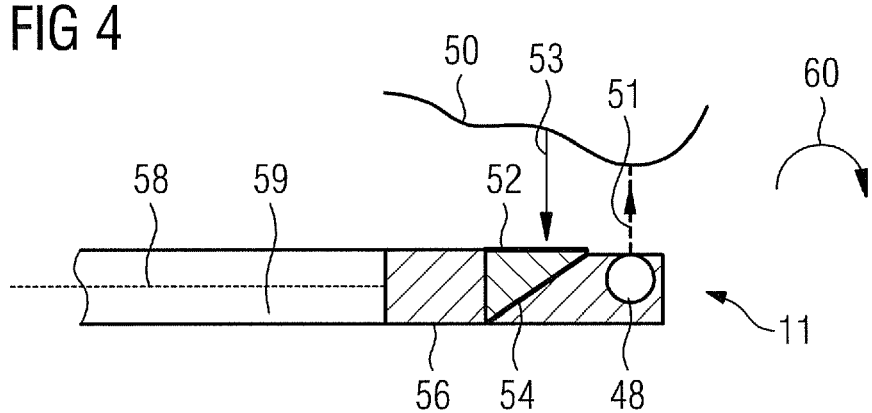
FIG. 4 shows a detailed diagram of an optical sensor with a lateral/radial observation direction.

FIG. 4 shows a CMOS-based optical sensor. A light source 48, in this instance a high-performance micro-LED, illuminates the vessel wall 50, which encloses the blood pump 1 and specifically the imaging sensor 11 an a roughly annular manner (transmitted light 51). Light 53 reflected off the vessel wall 50 passes through a lens 52 to a reflective mirror 54 (or even a prism for example with a similar mode of operation or beam guidance) and from there to the actual CMOS image detector 56. The arrangement according to FIG. 4 is thus configured for a radial viewing direction (relative to the center axis 58 of the blood pump 1). A rotational movement about the center axis 58 brought about with the aid of the drive shaft 59, as shown by the arrow 60, allows the full lateral 360° field of vision to be covered.

Figure 5:
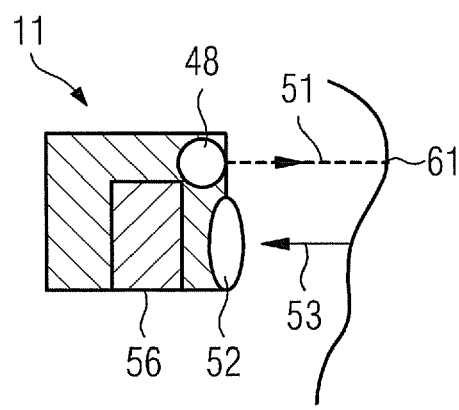
FIG. 5 shows a detailed diagram of an optical sensor with a forward observation direction.

Alternatively FIG. 5 shows an example of a configuration of light source 48, lens 52 and CMOS image detector 56, which allows forward observation, which is of particular benefit when the blood pump 1 is being advanced through a blood vessel. An obstacle 61 in the forward direction, which may impede the further advance, can thus be identified. The two variants in FIG. 4 and FIG. 5 can optionally also be combined to provide a particularly comprehensive field of vision or image recording field in practically all directions.

Figure 6:
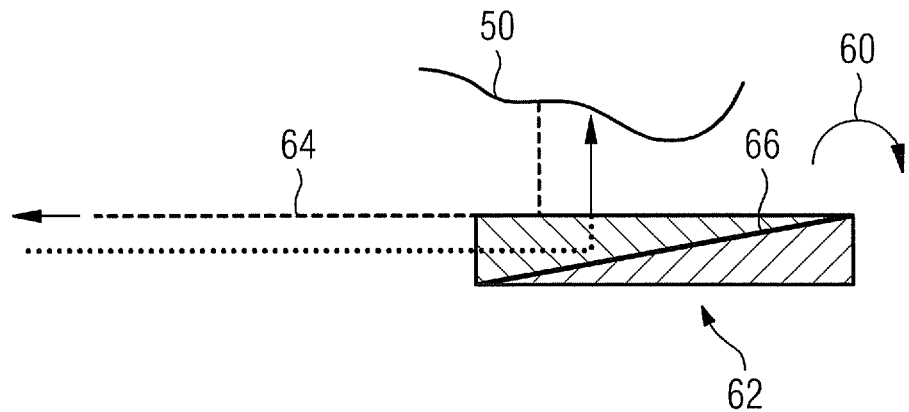
FIG. 6 shows a detailed diagram of a sensor head for OCT or LCI imaging with a lateral/radial observation direction.
Figure 7:
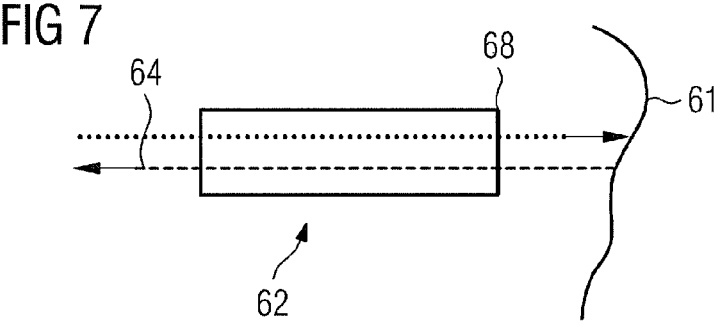
FIG. 7 shows a detailed diagram of a sensor head for OCT or LCI imaging with a forward observation direction.

The above-mentioned observation directions, namely radial/lateral and forward, can also be achieved with other sensor types. For example FIG. 6 shows a configuration of an OCT or LCI sensor head 62 for radial emission and radial receiving and FIG. 7 for forward emission and receiving. More specifically the reference character 62 only identifies the part of the sensor responsible for coupling the light into and out of the optical waveguide or the sensor head; the actual interferometric evaluation and image generation take place outside the blood pump 1. The beam path of the coupled-out and reflected light beams, which is influenced by the reflective minor 66 and the lens 68, is shown in each instance.

An IVMRI sensor or IVUS sensor can also be similarly configured.

Figure 8:
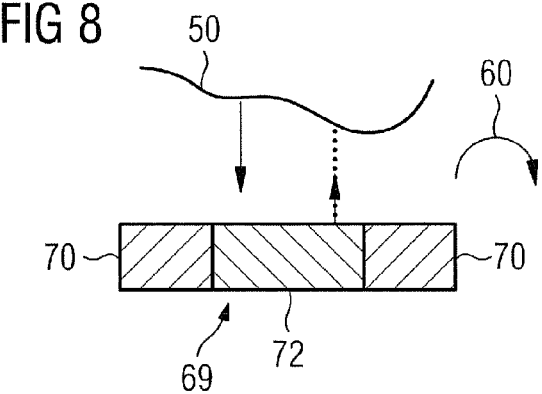
FIG. 8 shows a detailed diagram of a sensor for IVMRI imaging with a lateral/radial observation direction.
Figure 9:
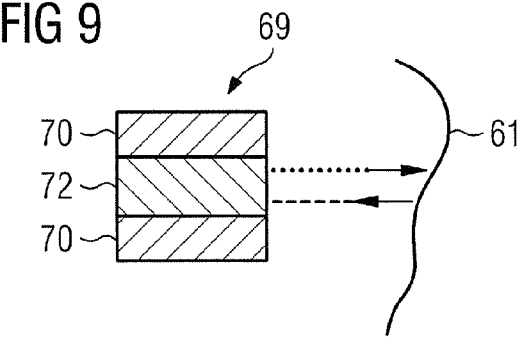
FIG. 9 shows a detailed diagram of a sensor for IVMRI imaging with a forward observation direction.

FIG. 8 and FIG. 9 show schematic diagrams of IVMRI sensors 69 with permanent magnets 70 for the static magnetic field and transmit/receive coils 72. The IVMRI sensor 69 shown in FIG. 8 is designed for radial recordings of image data and the IVMRI sensor 69 shown in FIG. 9 is designed for forward recordings of image data.

If the imaging sensor 11 is a magnetic resonance sensor, the individual sensors of the blood pump 1, for example the magnetic resonance sensor and the position sensor 18, are preferably temporally offset, read out in a clocked manner or the individual sensors are active with a temporal offset, to prevent them influencing one another as far as possible.

Figure 10:
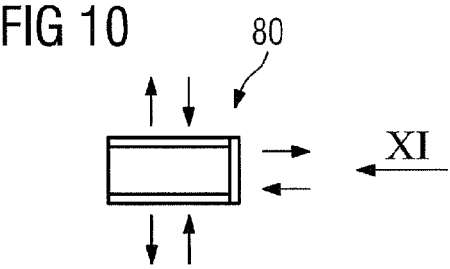
FIG. 10 shows a detailed diagram of an IVUs sensor with a lateral/radial and forward observation direction and FIG. 11 shows the view in the direction of the arrow XI from FIG. 10.

FIG. 10 shows an IVUS Sensor 80 for radial and forward emission and the corresponding receiving of ultrasonic waves. Instead of a single, optionally rotating ultrasonic sensor, an array of ultrasonic sensor elements with different "viewing directions" can be provided, these being activated, i.e. excited and interrogated, cyclically by way of a multiplexer for example, both for the radial and lateral emission and corresponding receiving of ultrasonic waves and for the forward emission and corresponding receiving of ultrasonic waves. The ultrasonic sensor elements can be disposed in an annular manner for the radial and lateral emission and the receiving of ultrasonic waves.

Figure 11:
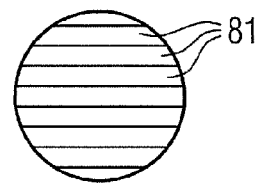

FIG. 11 shows the view in the direction of the arrow XI in FIG. 10. FIG. 11 shows a line-type arrangement of ultrasonic sensor elements 81, which are activated and interrogated cyclically with the aid of a multiplexer, for the forward emission and the corresponding receiving of ultrasonic waves.

The invention claimed is:

1. A blood pump for inserting into a heart of a patient, comprising:
   an imaging sensor disposed in a region of a distal end of the blood pump; and
   a drive shaft that rotates the imaging sensor,
   wherein the drive shaft drives a pump wheel of the blood pump, and
   wherein the drive shaft comprises a microtransmission.

2. The blood pump as claimed in claim 1, wherein the imaging sensor is aligned for recording a region that at least partially covers a spatial region around the distal end of the blood pump.

3. The blood pump as claimed in claim 1, wherein the imaging sensor is aligned for recording a region that at least partially covers a spatial region in front of the distal end of the blood pump.

4. The blood pump as claimed in claim 1, further comprising an outer sheath, wherein the imaging sensor is displaced longitudinally in relation to the outer sheath of the blood pump.

5. The blood pump as claimed in claim 1, wherein the imaging sensor is selected from the group consisting of: an ultrasonic sensor, a magnetic resonance sensor, an optical image sensor, a Complementary Metal Oxide Semiconductor image sensor, an Optical Coherence Tomography image sensor, an Low Coherence Interferometry image sensor, an Near-Infrared Diffuse Reflectance Spectroscopy image sensor, and an Optical Frequency Domain Imaging image sensor.

6. The blood pump as claimed in claim 1, wherein a plurality of imaging sensors are disposed in a ring or line.

7. The blood pump as claimed in claim 6, wherein the imaging sensors are cyclically readout by a multiplexer.

8. The blood pump as claimed in claim 1, further comprising a position sensor that determines a position of the blood pump in a body of the patient.

9. A medical apparatus, comprising:
   a blood pump comprising an imaging sensor disposed in a region of a distal end of the blood pump that records an image of a patient;
   an image processing and playback device disposed outside the blood pump and a body of the patient;
   a signal line that connects the imaging sensor of the blood pump to the image processing and playback device so that the image is transmitted to the image processing and playback device in real time; and
   a drive shaft that rotates the imaging sensor,
   wherein the drive shaft drives a pump wheel of the blood pump, and
   wherein the drive shaft comprises a microtransmission.

10. A method for assisting a positioning of a blood pump in a heart of a patient, comprising:
   recording an image inside a body of the patient using an imaging sensor disposed in a region of a distal end of the blood pump; and
   transmitting the image in real time to an image processing and playback device disposed outside a body of the patient,
   wherein the imaging sensor is rotated by a drive shaft,
   wherein the drive shaft drives a pump wheel of the blood pump, and
   wherein the drive shaft comprises a microtransmission.

* * * * *